United States Patent [19]
Errico et al.

[11] Patent Number: 5,885,284
[45] Date of Patent: Mar. 23, 1999

[54] HINGED VARIABLE LENGTH CROSS-LINK DEVICE

[75] Inventors: Thomas J. Errico, Summit; James D. Ralph, Oakland; Steven Tatar, Montville, all of N.J.

[73] Assignee: Third Millennium Engineering, L.L.C., Summit, N.J.

[21] Appl. No.: 677,812

[22] Filed: Jul. 11, 1996

[51] Int. Cl.$^6$ ................................................. A61B 17/70
[52] U.S. Cl. ................................................. 606/61; 606/72
[58] Field of Search ................................ 606/61, 60, 63, 606/73, 64, 72

[56] References Cited

U.S. PATENT DOCUMENTS

| | | | |
|---|---|---|---|
| 5,261,907 | 11/1993 | Vignaud et al. | 606/61 |
| 5,306,275 | 4/1994 | Bryan | 606/61 |
| 5,312,405 | 5/1994 | Korotko et al. | 606/61 |
| 5,368,984 | 11/1994 | Martin et al. | 606/61 |

Primary Examiner—Guy V. Tucker
Assistant Examiner—Daphna Shai

[57] ABSTRACT

A compression locking variable length cross-link device having a pair of rod hooking elements, each having coupling ends which are attachable to a rod. The opposing ends of the first of these elements includes a pair of extending members each having a hole; the holes being mutually co-linear. The opposing element of the second element includes a single extending member which has an elongated hole, such that when it is disposed between the pair of extending members of the first element, a linear passage is defined through the three holes. A hinge post is disposed in the co-linear passage; the post having a threaded top portion. The elongated hole permits the first and second elements to be translated relative to one another with the hinge post in place. A nut is engageable with the threaded top of the post, such that if tightened, the pair of extending members deflect inwardly into contact with the single extending member of the second element to crush lock the elements together. Various embodiments include features which permit enhanced rotationalability.

5 Claims, 6 Drawing Sheets

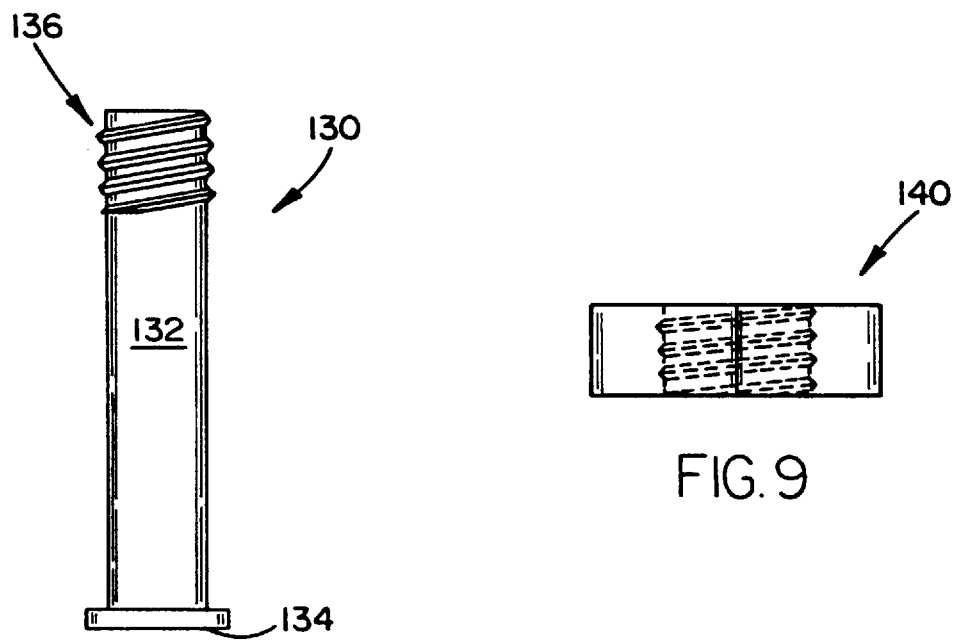
FIG.8
FIG.9
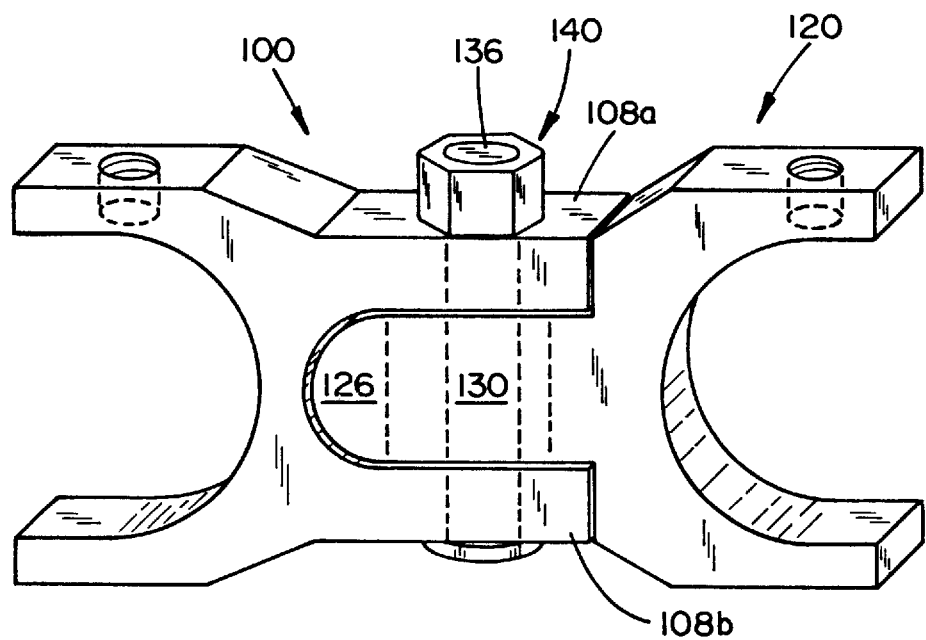
FIG.10

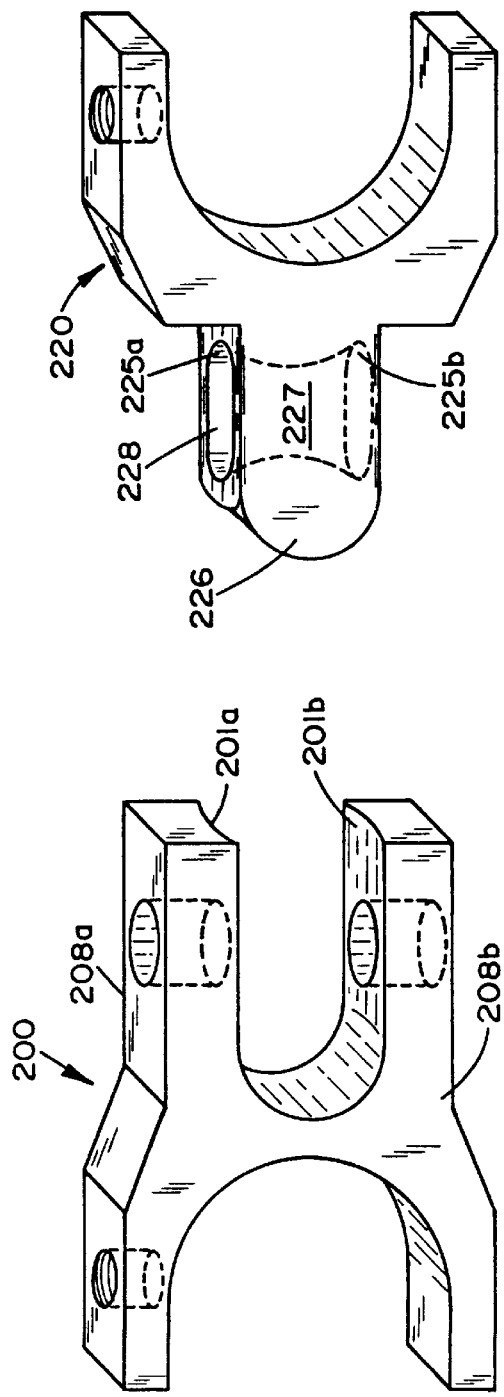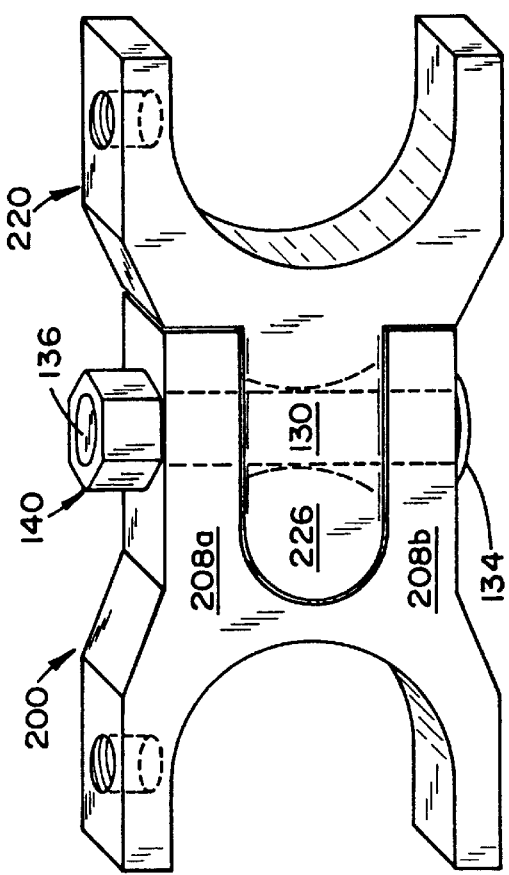

HINGED VARIABLE LENGTH CROSS-LINK DEVICE

BACKGROUND OF THE INVENTION

1. Field of the Invention

This invention relates generally to a mechanical cross-link device for use with dual rod orthopaedic implant apparatus. More particularly, this invention relates to a novel device which is fixed to each rod of a dual rod implant apparatus, where the rods are closely spaced, and enhances the rigidity of the apparatus.

2. Discussion of the Prior Art

The bones and connective tissue of an adult human spinal column consist of an upper portion (the cervical, thoracic, and lumbar regions) having more than 20 discrete bones, and a lower portion which consists of the sacral bone and the coccygeal bodies. The bones of the upper portion are generally similar in shape, the size of the bones progressively varying from small to large downwardly along the spine.

The vertebrae are coupled to one another by a tri-joint complex consisting of an anterior disc and the two posterior facet joints, the anterior discs of adjacent bones being cushioned by cartilage spacers referred to as intervertebral discs. Referring now to FIGS. 1, 2 and 3, top, lateral, and posterior views of a typical vertebral bones of the spinal column are shown. The spinal cord is housed in the central canal 10, protected from the posterior side by a shell of bone called the lamina 12. The lamina 12 has three large protrusions, two of these extend laterally from the side ends thereof and are referred to as the transverse processes 14. The third extends back and down from the center of the lamina and is called the spinous process 16. The lamina 12 defines an arched shape about the posterior of the spinal cord, the arched shape having lateral portions 13a,13b which are generally straight, and which meet beneath the spinous process at a curved surface 15.

The anterior portion of the spine comprises a set of generally cylindrically shaped bones which are stacked one on top of the other. These portions of the vertebrae are referred to as the vertebral bodies 20, and are each separated from the other by the intervertebral discs 22. Pedicles 24 are bone bridges which couple the anterior vertebral body 20 to the corresponding lamina 12 and posterior elements 14,16.

Referring specifically to FIG. 3, the stacking of vertebrae is shown from the posterior. From the posterior, each vertebra is coupled to the one above and below via facet joints 19 on either side of an opening into the spinal canal 10.

In its entirety, the spinal column is highly complex in that it houses and protects critical elements of the nervous system which have innumerable peripheral nerves and arterial and venous bodies in close proximity. In spite of these complexities, the spine is a highly flexible structure, capable of a high degree of curvature and twist through a wide range of motion. Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column.

A variety of systems have been disclosed in the art which achieve this immobilization by implanting artificial assemblies in, or on, the spinal column. These assemblies may be classified by their position relative to the spine, as anterior, posterior, or lateral implants. Anterior and lateral assemblies generally comprise short structures which support only a few adjacent vertebral bodies. Conversely, posterior implants often comprise pairs of elongate vertically aligned rods for stabilizing both short and long segments of the spine. Such posterior rods are coupled to the back of the spinal column via hooks which slip under the lamina, means for attaching to the transverse process, and/or by screws which are inserted through the pedicle bone. In order to provide enhanced torsional rigidity, these apparatuses generally include cross-linking devices which couple the rods together transverse to the axis (vertical axis) of the apparatuses.

Referring now to FIG. 4, U.S. Pat. No. 5,005,562 to Cotrel teaches such a dual rod apparatus which includes cross-link devices 38a,38b. These cross-link devices 38a,38b each include a pair of U-shaped gripping element 35a,35b which may receive the rod 30a,30b respectively. Each of the gripping elements includes a first threaded hole which extends from the outer lateral surface into the inner surface of the U-shaped rod receiving region. The gripping elements 35a,35b are fixed to the rods 30a,30b by set screws 37a,37b which are positioned in the first holes such that tightening of the set screws locks the rod 30a,30b in the gripping element. The gripping elements 35a,35b are coupled together by a threaded rod 33 which permits the gripping elements to be selectively spread or brought closer together, in accordance with the relative position of the rods 30a,30b. The threaded rod 33 extends through a second set of threaded holes in the gripping elements 35a,35b.

The bulkiness of each of the gripping elements 35a,35b, required so that it may receive the threaded rod 33, is difficult for the surgeon to use easily under operative conditions. This difficulty is dramatically enhanced by the closeness of the rods in the cervical spine. The size of the gripping elements, and the relative position of the set screws often cause substantial difficulty with respect to the tightening of same because of their positions relative to the operative access. This bulkiness also reduces available bone graft surface area, which is critical for a successful fusion and long term immobilization. In addition, in order for a surgeon to selectively vary the spread of the gripping elements 35a,35b, one of the gripping elements must be rotated relative to the other, thus requiring the cross-link to be removed (loosening the set screws and withdrawing the device entirely from the operative site). This is particularly burdensome with respect to providing the surgeon with the ability to apply an inward force to the rods 30a,30b as the spread may not be varied in situ.

It is therefore, a principal object of the present invention to provide a new and novel cross-link device which provides a less bulky profile, therein permitting its inclusion in the cervical spine wherein the rods are closely spaced.

It is further an object of the present invention to provide a cross-linking device which admits increased area for bone grafting.

It is also an object of the present invention to provide a cross-link device which provides the surgeon with the ability to lock the device to the rods more easily than prior cross-link devices.

It is also, therefore, an object of the present invention to provide a cross-link device which provides the surgeon with the ability to vary the spread of the rod gripping portions in situ, so that in doing so, the surgeon is not required to withdraw the device from the patient.

It is correspondingly an object of the present invention to provide a cross-link device which permits the surgeon to use the variable spread of the device to impart an inward force relative to the two rods, which is a desirable feature for the purposes of enhanced rotational stability.

Other objects of the present invention not explicitly stated will be set forth, and will be more clearly understood, in conjunction with the descriptions of the preferred embodiments disclosed hereafter.

SUMMARY OF THE INVENTION

The preceding objects of the invention are achieved by the present invention which is a hinged variable length crosslink device which may be affixed to closely spaced rods of a dual rod implant apparatus. The present invention may be practiced in a variety of different embodiments; the several enclosed herein being representative of preferred ones of the invention.

The device comprises a pair of C-shaped rod hooking elements so as to receive therein and/or seat against and hook to the lateral inside surfaces of the rods of a dual rod apparatus. Set screws are incorporated into the hooking portions to lock to the rod. The elements couple together to permit variable length and angulability in the following manner. At the opposite end of the first element from the C-shaped rod coupling site, there is a pair of upper and lower extending members each having a hole therethrough, said holes being co-linear. At the opposite end of the second element there is a single extending portion which seats between the upper and lower extending members of the first element. An elongated hole (slot) is provided in this single extending portion which is co-linear with the two holes in the first element such that a continuous axial passage is provided through relative translation and angulation of the two elements. This coupling is a hinge-type wherein the hole in one element (herein the second element) is elongated into a slot such that the two elements may be angulated or spread apart independently.

The shaft which is disposed in the axial passage formed by the co-linear holes of the first and second elements includes a thickened bottom end portion having a diameter greater than the hole in the lower extending member of the first element. This thickened portion prevents the shaft from being removable through the top of the mutual passageway formed by the coupled elements. The top of the shaft, which extends above the hole in the upper extending member of the first element, includes a threading. When engaged by a nut thereon, the contact pressure of the nut onto the upper extending member and the oppositely directed pressure from the thickened portion at the bottom of the shaft against the lower extending portion, provides a deflection of the extending elements toward one another, and onto the single extending members of the second element disposed therebetween. Continued tightening of the nut causes the coupled elements to be locked to one another. Inasmuch as prior to tightening the slot hole in the second element permits lateral translation of the two elements relative to one another, and because the hinge-type engagement permits a degree of angulability, the tightened cross-link may maintain a variety of different conformations.

It shall be understood that in an alternate embodiment, the holes of the upper and lower extending members may be elongated (slots) rather than, or in addition to, the hole in the single extending member of the second element.

It is further contemplated that a variation of the present invention may be provided in which the inner (facing) surfaces of the upper and lower extending members are concave, and the single extending member of the second element is cylindrical. In such an embodiment the hole in the single extending member may be conical such that the second element may be rotated through a range of angles relative to the first element.

BRIEF DESCRIPTION OF THE DRAWINGS

FIG. 8 is a side view of a post which is used in conjunction with an embodiment of the present invention;

FIG. 9 is a side view of a top locking nut which threadably mates to an upper portion of the post of FIG. 8;

FIG. 10 is a side perspective view of a fully assembled embodiment of the present invention comprising all of the elements illustrated in FIGS. 5–9;

FIG. 11 is a side perspective view of an alternative first rod hooking element;

FIG. 12 is a side perspective view of an alternative second rod hooking element;

FIG. 13 is a side perspective view of a fully assembled alternative embodiment of the present invention which includes the elements illustrated in FIGS. 6, 8, 9, 11, and 12.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 2:
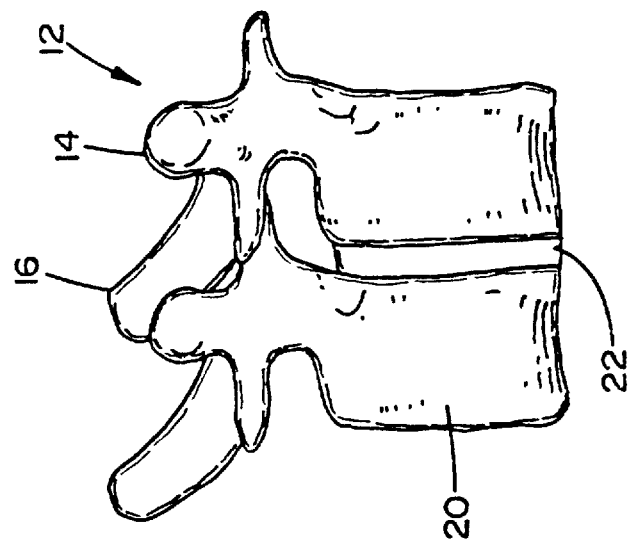
FIG. 2 is a side view of a sequence of vertebrae of the human spine.
Figure 1:
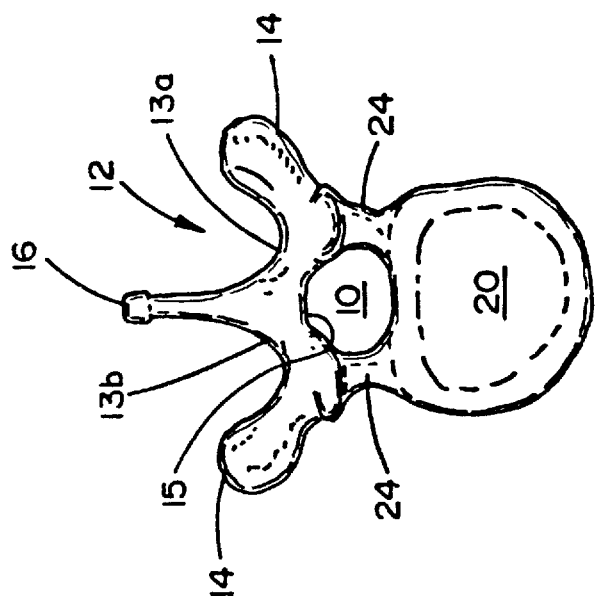
FIG. 1 is a top view of a vertebra of the human spine.
Figure 3:
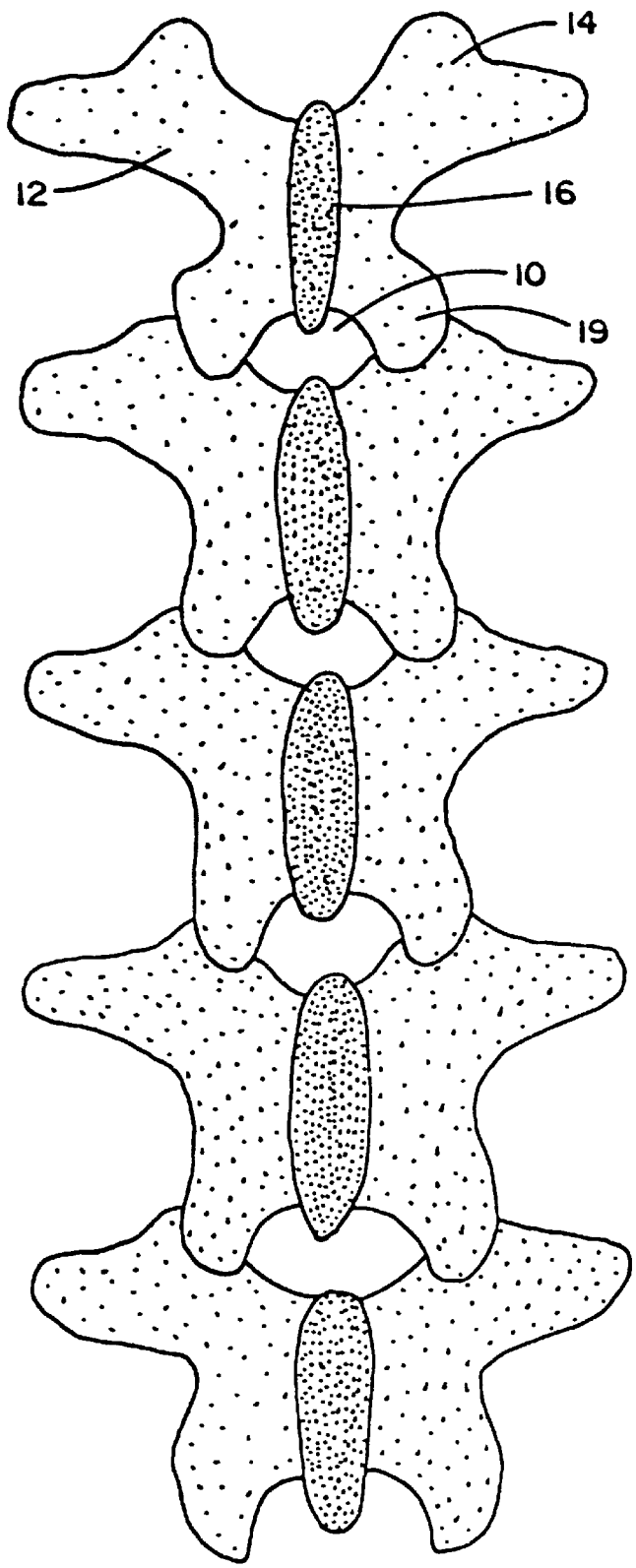
FIG. 3 is a posterior view of a sequence of vertebrae of the human spine.
Figure 4:
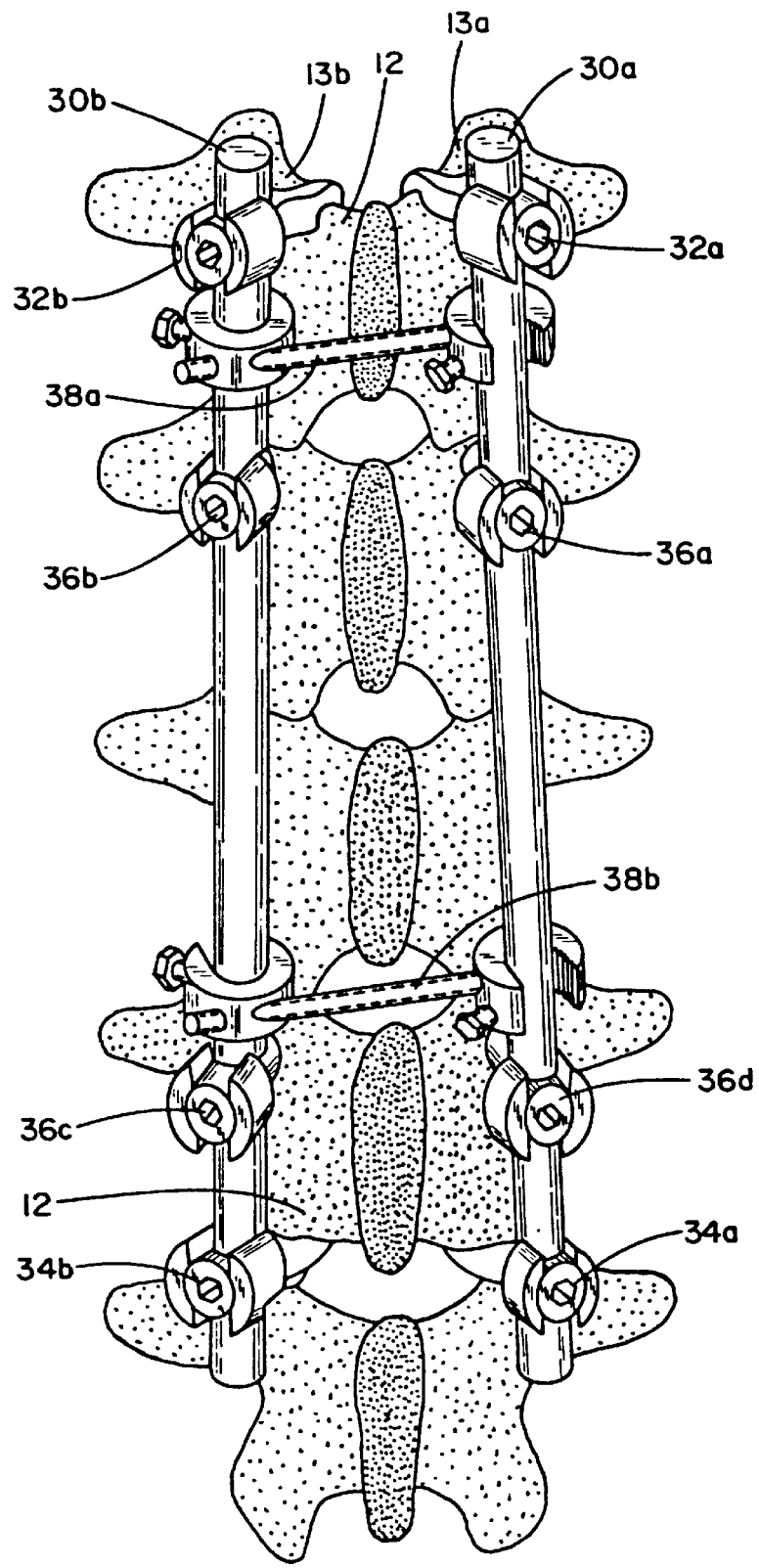
FIG. 4 is a posterior view of a dual rod apparatus of a prior art instrumentation as set forth in U.S. Pat. No. 5,005,562 to Cotrel, including cross-link devices.
Figure 5:
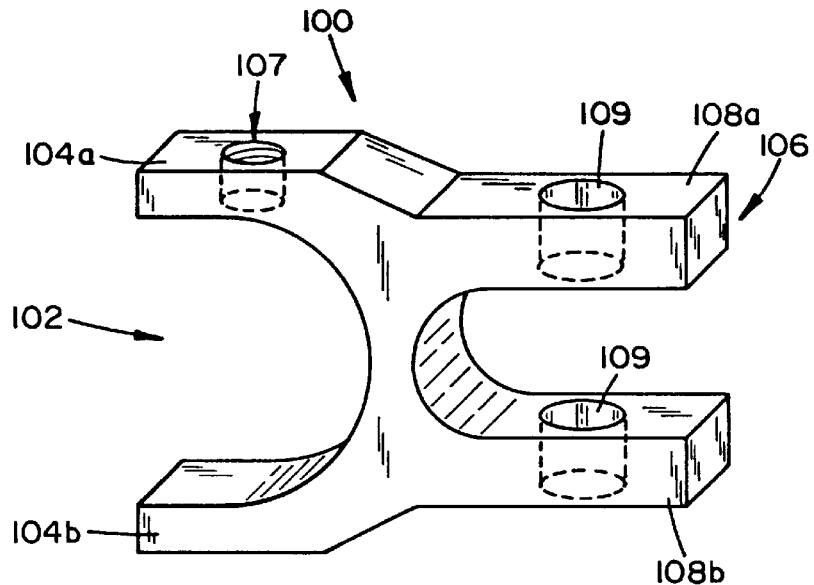
FIG. 5 is a side perspective view of a first rod hooking element which is an aspect of the present invention.

Referring now to FIG. 5, a first rod hooking element 100 of the first embodiment of the present invention is provided in a side perspective view. As with all elements of this invention, the material of which this rod hooking element may comprise a high strength material, for example medical grade steel or titanium compounds, which has been found ideally suited for implantation into the human body. The first end 102 of the element 100 is C-shaped for seating against a rod. More specifically, the C-shaped end 102 comprises a pair of spaced apart extending members 104a,104b which define therebetween the rod receiving site. One of the pair of spaced apart extending members 104a includes a threaded through hole 107 for receiving a threaded set screw 110 (see FIG. 6). This set screw 110 is employed, once the element 100 has been properly positioned, to lock the element 100 to the rod.

The other end 106 of the element 100 comprises spaced apart upper and lower extending members 108a,108b. These members are substantially parallel, and each have a through hole 109; said through holes 109 being co-linear and substantially orthogonal to both the extending axis of the parallel members 108a,108b, and to the anticipated axis of the rod to which the element 100 is to be coupled.

Figure 6:
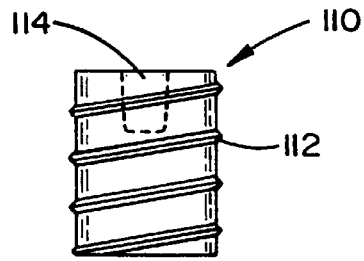
FIG. 6 is a side view of a set screw which is another aspect of the present invention.

Referring now to FIG. 6, the set screw 110, which is utilized to lock the rod in the element 100 via compression is shown in a side view. The set screw 110 comprises a cylindrical slug having a surface threading 112 which is ideally suited to the threading of the through hole 107. The screw 110 further includes a recess 114 in the top thereof, the recess having an internal conformation which may be engaged by a suitable tool for applying a torsional force thereto, for example a slot for a screwdriver or a hexagonally angled interior wall for an allen wrench.

Figure 7:
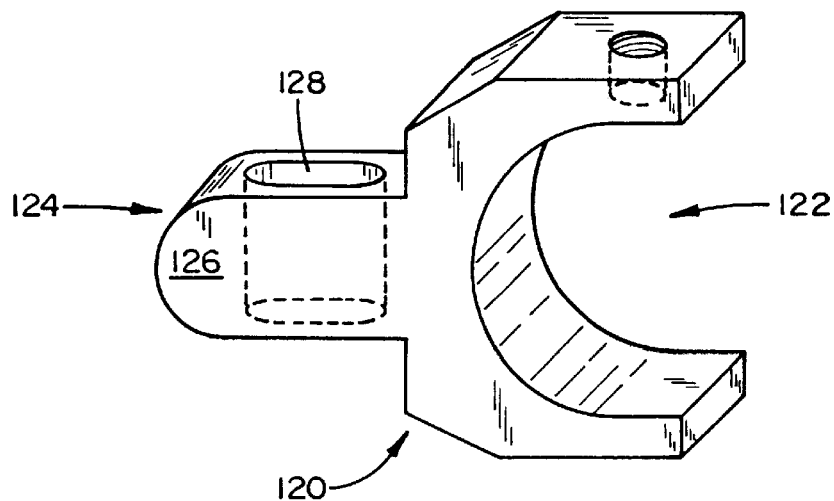
FIG. 7 is a side perspective view of a second rod hooking element which is an aspect of the present invention.

Referring now to FIG. 7, the second element 120, which is coupled to the other rod of the dual rod apparatus, is shown in a side perspective view. More specifically, the second element 120 comprises a first end 122 which is substantially identical to the first rod coupling end 102 of the first element 100. The second end 124, however, comprises a single extending member 126 which has a single elongated through hole 128 therethrough. This single extending member 126 has a thickness which is approximately equivalent to the distance between the upper and lower extending members 108a,108b of the first element 100. This permits the disposition of the single extending member 126 between the upper and lower members 108a,108b. The elongated through hole 128 is thereby positioned co-linearly with the holes 109 in the upper and lower extending memebers 108a,108b. Because the through hole 128 in the single extending member 126 is elongated (it is a slot), the first and second elements 100,120 may be translated relative to one another so as to widen or narrow the overall spacing between the rod seating ends to accommodate rod pairs of different spacings.

Referring now to FIGS. 8 and 9, the hinge post (or shaft) 130 and the locking nut 140 are shown in side and side cross-section views, respectively. Specifically with respect to FIG. 8, a hinge post 130 is provided to be inserted through the aligned through holes 109,128 of the first and second elements 100,120. The hinge post 130 has a cylindrical body 132 of generally constant diameter. The bottom end 134 of the post 130, however, is thickened (wider) such that its diameter is larger than the hole 109 in the lower extending member 108b. The upper end 136 of the post 130 is threaded. The post 130 is long enough so that, during assembly, it may be inserted upwardly through the co-linear holes 109,128 such that the threaded portion extends above the hole 109 in the upper extending member (until the widened bottom end 134 of the post 130 comes into contact with the bottom of the lower extending member 108b). The locking nut 140 is then threadably advanced onto the threaded upper portion 136 of the post 130.

Referring now also to FIG. 10, in which the fully assembled first and second elements 100,120, the post 130, and the nut 140 are shown, the function and use of this embodiment of the present invention is shown. Prior to full tightening of the nut 140 downwardly onto the post 130 (and thereby into contact with the upper extending member) the first and second members are capable of semi-independent motion, such that the elements may be pulled apart to a wider conformation, pushed together to a more narrow conformation, and even angled relative to one another so that rods which are not parallel may each be fully seated in the rod attaching ends thereof. Once the proper separation and angulation of the assembly has been established (and the rods properly seated in the rod coupling ends) the set screws 110 are tightened to lock the assembly to the rods. Once the device is coupled to the rods, the locking nut 140 is advanced further along the upper threaded portion 136 of the post 130 until it contacts the top surface of the upper extending member 108a. Continued rotation of the nut 140 causes the widened portion 134 of the post to apply upward pressure against the lower surface of the lower extending member 108b. The upper and lower extending members 108a,108b are thereby compressed together against the upper and lower surfaces, respectively, of the single extending member 126, thereby crush-locking the assembly together.

Referring now to FIGS. 11, 12, and 13, an alternative variation of the present invention is described. More specifically, this embodiment includes sufficiently altered shaped features so as to permit independent rotation of one element relative to the other. More specifically, with respect to the first element 200 shown in FIG. 11, the inner surfaces 201a,201b of the upper and lower extending members 208a,208b are concavely contoured to approximate arcs of a cylindrical member (or at least partially cylindrical member. Referring now to FIG. 12, the single extending member 226 of the second element is cylindrical. (It is understood that it is not required that the member be continuously cylindrical, but rather, comprises upper and lower surfaces thereof which are curvate so that it may slide through a continuous range of angles between the upper and lower members 208a,208b.)

In order that the assembly function properly, i.e., that the rotational advance of the locking nut 140 along the threaded portion 136 of the post 130 lock the assembly in position, while still being able to rotate in the axial direction and angulate, it is desireable that the through hole 228 be conical. By conical, it is meant that the hole 228 have a wider diameter at either opening 225a,225b, and a narrow diameter throat 227 therebetween. The diameter of the throat 227 is equal to the diameter of the post 130, such that the second element may rotate axially with the post therein (prior to final compression locking of the single extending member 226 between the upper and lower extending members 208a,208b by advance of the nut).

While there have been described and illustrated cross-link devices for coupling dual rods of orthopaedic apparatus together and providing enhanced stability thereto, it will be apparent to those skilled in the art that variations and modifications are possible without deviating from the broad spirit and principle of the present invention which shall be limited solely by the scope of the claims appended hereto.

We claim:

1. A variable length cross-link device for use with orthopaedic rod apparatuses having a pair of rods, comprising:

first and second rod hooking elements each having first and second ends, said first ends of each having means for securing to alternative ones of said pair of rods;

said second end of said first element having spaced apart upper and lower extending members, said members defining therebetween a receiving space, each of said members having a through hole, said through holes being mutually co-linear;

said second end of said second element having an extending member positionable in said receiving space, and having an elongated through hole positionable co-linearly with said through holes of said first element, forming therewith a passage, a post element positionable in said passage;

a locking nut selectively engageable and tightenable on said post, whereby prior to said selective tightening the first and second elements may be translated relative to one another via the movement of said post in said elongated through hole of said second element, and whereby selective tightening of said locking nut causes said upper and lower extending members to deflect and crush lock against said extending member of said second element.

2. The device as set forth in claim 1, wherein the rod securing means of the first ends of the first and second elements comprise C-shaped cupping portions having a threaded hole therethrough, and a set screw disposed in said threaded hole, and whereby advancement of said set screw in said hole against a rod seated in said cupping portion locks said element to said rod.

3. The device as set forth in claim 1, wherein said upper and lower extending members of said first element comprise mutually facing surfaces which are concave.

4. The device as set forth in claim 3, wherein said extending member of said second element comprises a curvate outer surface, whereby mutual engagement of the extending member of the second element between the upper and lower extending members of the first element permits independent rotational movement prior to the locking of the two elements together.

5. The device as set forth in claim 4, wherein said elongate hole in said extending member of said second element has a conical cross-sectional conformation such that said first and second elements may rotate independently with the hinge post disposed through the mutually co-linear holes of both elements.

* * * * *